(12) United States Patent
Kesari et al.

(10) Patent No.: US 6,394,107 B1
(45) Date of Patent: May 28, 2002

(54) USE OF FLUORINATED KETONES AS WET CLEANING AGENTS FOR VAPOR REACTORS AND VAPOR REACTOR COMPONENTS

(75) Inventors: Susrut Kesari, St. Paul; Jason M. Kehren, Woodbury; Richard M. Minday, Stillwater, all of MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/841,340

(22) Filed: Apr. 24, 2001

(51) Int. Cl.$^7$ .................................................. B08B 9/00
(52) U.S. Cl. ..................... 134/22.1; 134/2; 134/22.11; 134/22.14; 134/22.19; 134/36; 134/42
(58) Field of Search .................... 134/2, 22.1, 22.11, 134/22.14, 22.19, 36, 42

(56) References Cited

U.S. PATENT DOCUMENTS

| | | | | |
|---|---|---|---|---|
| 3,185,734 A | * | 5/1965 | Fawcett et al. | ............. 260/586 |
| 4,136,121 A | * | 1/1979 | Martini et al. | .......... 260/593 H |
| 5,399,718 A | * | 3/1995 | Costello et al. | ............. 549/266 |
| 5,466,877 A | * | 11/1995 | Moore | ........................ 562/852 |
| 5,998,671 A | * | 12/1999 | Van Der Puy | ............. 568/411 |

FOREIGN PATENT DOCUMENTS

| | | | | |
|---|---|---|---|---|
| JP | 2869432 | * | 3/1999 | |
| JP | 2952414 | * | 9/1999 | |
| JP | 200-248363 | * | 9/2000 | |
| JP | P2000-265197 A | * | 9/2000 | |

* cited by examiner

*Primary Examiner*—Sharidan Carrillo

(57) ABSTRACT

A method for cleaning a vapor reactor by applying a liquid cleaning agent comprising a fluorinated ketone having about 5 to about 10 carbon atoms and up to two hydrogen atoms is described. The fluorinated ketone has low global warming potential.

17 Claims, No Drawings

USE OF FLUORINATED KETONES AS WET CLEANING AGENTS FOR VAPOR REACTORS AND VAPOR REACTOR COMPONENTS

FIELD OF INVENTION

The invention relates to the use of fluorinated ketones as wet cleaning agents for vapor reactors and vapor reactor parts.

BACKGROUND OF INVENTION

The emission of global warming gases has received worldwide attention. The goal of the Kyoto Protocol, established at the United Nations Conference on Global Warming, was to lower emissions of carbon dioxide, methane, nitrous oxide, perfluorocarbon (PFC), hydrofluorocarbon (HFC), and $SF_6$ to pre-1990 levels. Additionally, most manufacturers of semiconductors in the United States have signed a Memorandum of Understanding with the Environmental Protection Agency pledging to evaluate options for reducing PFC emissions.

Chemical vapor deposition chambers, physical vapor deposition chambers, and etching chambers are widely used in the semiconductor industry in connection with the manufacture of various electronic device and components. Such chambers use reactive gases or vapors to deposit, pattern, or remove various dielectric and metallic materials. Over time, undesirable deposits, typically fluoropolymers containing carbon, fluorine, hydrogen and oxygen atoms, inevitably build up on both the walls and parts of the chamber. These deposits are a source of potential contamination for the product being manufactured in the chamber and must be removed periodically. Perfluorocarbon gases such as $C_2F_6$ and $C_3F_8$ as well as perfluorinated nitrogen compounds such as $NF_3$ have been used extensively for in situ plasma cleaning of the chamber. However, these gaseous materials are extremely stable compounds that contribute to global warming and are difficult to trap or treat with gas scrubbers.

The chamber walls and components can be cleaned using various liquid chemicals. The liquid cleaning agents currently used include water, various hydrocarbons such as acetone or isopropanol, and various fluorochemicals such as perfluorocarbons, hydrofluorocarbons, and hydrofluoro ethers. Water and hydrocarbons do not readily dissolve the fluoropolymer residue. Additionally, water requires long drying times and the hydrocarbons are flammable; these are both undesirable properties for a cleaning agent. Some fluorochemicals have the potential to contribute to global warming, another undesirable property for a cleaning agent.

This invention provides a method for removing deposits that build up on the walls and parts of a chemical vapor deposition chamber, a physical vapor deposition chamber, or an etching chamber using a liquid cleaning agent comprising a fluorinated ketone. The fluorinated ketones of this invention perform as well as the liquid perfluorochemicals traditionally used in the semiconductor industry but have lower global warming potential.

SUMMARY OF INVENTION

This invention provides a method of cleaning the walls and parts of a chemical vapor deposition chamber, a physical vapor deposition chamber, or an etching chamber using a liquid cleaning agent comprising a fluorinated ketone compound containing 5 to 10 carbon atoms. The cleaning agent can be a perfluoroketone, a compound in which all of the hydrogen atoms on the carbon backbone are replace with fluorine. Alternatively, the fluorinated ketone cleaning agent can have up to two hydrogen atoms and up to two non-fluorine halogen atoms including bromine, chlorine, and iodine attached to the carbon backbone. One or more heteroatoms can interrupt the carbon backbone of the molecule. The cleaning agent can also include an auxiliary halogenated compound that is miscible with the fluorinated ketone. Preferably, the auxiliary halogenated compound is a hydrofluoroether. The cleaning agent can be applied by wiping, spraying, soaking, and the like.

DETAILED DESCRIPTION OF ILLUSTRATIVE EMBODIMENTS OF THE INVENTION

This invention provides a method of cleaning a chemical vapor deposition chamber, a physical vapor deposition chamber, or an etching chamber using a liquid cleaning agent comprising a fluorinated ketone compound having 5 to 10 carbon atoms, preferably 6 to 8 carbon atoms. The fluorinated ketones typically are liquids at room temperature with boiling points up to about 150° C. Preferably, the fluorinated ketone is a perfluoroketone.

As used herein, the term "vapor reactor" includes chemical vapor deposition chambers, physical vapor deposition chambers, and etching chambers. Such chambers use reactive gases or vapors to deposit, pattern, or remove various dielectric and metallic materials. Vapor reactors are widely used in the semiconductor industry to manufacture a variety of electronic devices and components. Typically, gaseous perfluorocarbons such as $CF_4$, $C_2F_6$, and $C_3F_8$ are used to etch various dielectric and metallic materials. The perfluorocarbons are usually mixed with oxygen gas and a radio frequency plasma is generated resulting in the formation of various radicals such as fluorine, carbon difluoride, carbon trifluoride, and the like. These radicals can undergo further reactions to form various fluoropolymers. The fluoropolymers deposit on the reactor walls and parts along with various other by-product of the manufacturing process. These by-products can include, for example, silicon-based residues and metallic residues such as tungsten, aluminum, and the like. Periodically, the vapor reactor needs to be cleaned to remove the fluoropolymers and other residues to avoid contaminating the product being prepared.

The traditional approach to removing the deposits has been to use various liquid cleaning agents. The liquid cleaning agents currently used include water, various hydrocarbons such as acetone or isoproponal, and various fluorochemicals such as perfluorocarbons, hydrofluorocarbons, and hydrofluoroethers. Water and hydrocarbons do not readily dissolve the fluoropolymer residue. Additionally, water requires long drying times and the hydrocarbons are flammable; these are both undesirable properties for a cleaning agent. The invention provides an alternative approach that avoids these undesirable properties in a manner that is more environmentally friendly than at least some prior approaches. The fluoropolymers and other residue that deposit on the reactor walls and parts can be dissolved using a liquid fluorinated ketone cleaning agent having 5 to 10 carbon atoms. The method of cleaning a vapor reactor can be used to partially or completely replace the conventional cleaning process with gaseous perfluorocarbons. As used herein, the term "cleaning" refers to removing the unwanted deposits that build up over time on the walls and parts of a vapor reactor.

The fluorinated ketones of the invention typically have a total of 5 to 10 carbon atoms and preferably have 6 to 8 carbon atoms. The cleaning agent can be a perfluoroketone, a compound in which all of the hydrogen atoms on the carbon backbone are replaced with fluorine. Alternatively, the fluorinated ketone cleaning agent can have up to two hydrogen atoms and up to two non-fluorine halogen atoms including bromine, chlorine, and iodine attached to the carbon backbone.

Representative examples of perfluorinated ketone compounds suitable as cleaning agents include $CF_3(CF_2)_5C(O)CF_3$, $CF_3C(O)CF(CF_3)_2$, $CF_3CF_2CF_2C(O)CF_2CF_2CF_3$, $CF_3CF_2C(O)CF(CF_3)_2$, $(CF_3)_2CFC(O)CF(CF_3)_2$, $(CF_3)_2CFCF_2C(O)CF(CF_3)_2$, $(CF_3)_2CF(CF_2)_2C(O)CF(CF_3)_2$, $(CF_3)_2CF(CF_2)_3C(O)CF(CF_3)_2$, $CF_3(CF_2)_2C(O)CF(CF_3)_2$, $CF_3(CF_2)_3C(O)CF(CF_3)_2$, $CF_3(CF_2)_4C(O)CF(CF_3)_2$, $CF_3(CF_2)_5C(O)CF(CF_3)_2$, $CF_3CF_2C(O)CF_2CF_2CF_3$, perfluorocyclopentanone, and perfluorocyclohexanone.

Representative examples of fluorinated ketones with either one or two atoms other than fluorine attached to the carbon backbone include $CHF_2CF_2C(O)CF(CF_3)_2$, $CF_3C(O)CH_2C(O)CF_3$, $(CF_3)_2CFC(O)CF_2Cl$, $CF_2ClCF_2C(O)CF(CF_3)_2$, $CF_2Cl(CF_2)_2C(O)CF(CF_3)_2$, $CF_2Cl(CF_2)_3C(O)CF(CF_3)_2$, $CF_2Cl(CF_2)_4C(O)CF(CF_3)_2$, $CF_2Cl(CF_2)_5C(O)CF(CF_3)_2$, and $CF_2ClCF_2C(O)CF_2CF_2CF_3$.

The fluoroketones can also contain one or more heteroatoms interupting the carbon backbone. Suitable heteroatoms include, for example, nitrogen, oxygen, and sulfur atoms. Representative compounds include, for example, $CF_3OCF_2CF_2C(O)CF(CF_3)_2$ and $CF_3OCF_2C(O)CF(CF_3)_2$.

Fluoroketones can be prepared by known methods. One approach involves the dissociation of perfluorinated carboxylic acid esters of the formula $R_fCO_2CF(R_f')_2$ with a nucleophilic initiating agent as described in U.S. Pat. No. 5,466,877 (Moore). $R_f$ and $R_f'$ are fluorine or a perfluoroalkyl group. The fluorinated carboxylic acid ester precursor can be derived from the corresponding fluorine-free or partially fluorinated hydrocarbon ester by direct fluorination with fluorine gas as described in U.S. Pat. No. 5,399,718 (Costello et al.).

Perfluorinated ketones that are alpha-branched to the carbonyl group can be prepared as described in U.S. Pat. No. 3,185,734 (Fawcett et al.). Hexafluoropropylene is added to acyl halides in an anhydrous environment in the presence of fluoride ion. Small amounts of hexafluoropropylene dimer and/or trimer impurities can be removed by distillation from the perfluoroketone. If the boiling points are too close for fractional distillation, the dimer and/or trimer impurity can be removed by oxidation with alkali metal permanganate in a suitable organic solvent such as acetone, acetic acid, or a mixture thereof. The oxidation reaction is typically carried out in a sealed reactor at ambient or elevated temperatures.

Linear perfluorinated ketones can be prepared by reacting a perfluorocarbon acid alkali metal salt with a perfluorocarbon acid fluoride as described in U.S. Pat. No. 4,136,121 (Martini et al.) Such ketones can also be prepared by reacting a perfluorocarboxylic acid salt with a perfluorinated acid anhydride in an aprotic solvent at elevated temperatures as described in U.S. Pat. No. 5,998,671 (Van Der Puy).

All the above-mentioned patents describing the preparation of fluoroketones are incorporated by reference in their entirety.

The fluorinated ketone cleaning agent can be applied alone, in combination with another fluorinated ketone, or in combination with one or more auxiliary cleaning agents that are miscible with the fluorinated ketone. The auxiliary cleaning agents are typically halogenated compounds including, for example, hydrofluorocarbons, hydrochlorofluorocarbons, perfluorocarbons, perfluoropolyethers, hydrofluoroethers, hydrofluoropolyethers, hydrochlorofluoroethers, fluorinated aromatic compounds, chlorofluorocarbons, bromofluorocarbons, bromochlorofluorocarbons, hydrobromocarbons, iodofluorocarbons, and hydrobromofluorocarbons. Representative examples of auxiliary cleaning agents include $C_5F_{11}H$, $C_6F_{13}H$, $C_4F_9OCH_3$, $C_4F_9OC_2H_5$, $C_3F_7CF(OC_2H_5)CF(CF_3)_2$, $CF_3CH_2CF_2CH_3$, $CF_3CFHCFHCF_2CF_3$, $C_6F_{14}$, $C_7F_{16}$, $C_8F_{18}$, $(C_4F_9)_3N$, perfluoro-2-butyltetrahydrofuran, perfluoro-N-methylmorpholine, $HCF_2O(CF_2O)_n(CF_2CF_2O)_mCF_2H$ (where n is from 0 to 2, m is from 0 to 5, and the sum of n plus m is at least 1), $C_3F_7I$, benzotrifluoride, trans-1,2-dichloroethylene, and the like. Preferably, the auxiliary cleaning agent is a hydrofluoroether such as $C_4F_9OCH_3$, $C_4F_9OC_2H_5$, $C_3F_7CF(OC_2H_5)CF(CF_3)_2$, and the like.

The fluorinated ketone cleaning agents can be applied by, for example, by wiping, spraying, and immersion of the parts for soaking or dipping. The cleaning agent can be combined with an inert propellant such as nitrogen, argon, or carbon dioxide to direct the cleaning agent to specific surfaces that need cleaning. The cleaning agent can be applied at either ambient or elevated temperatures, for example, up to 150° C.

The perfluoroketones of the invention have much lower global warming potential (GWP) than the conventional perfluorocarbons used in the semiconductor industry. As used herein, "GWP" is a relative measure of the warming potential of a compound based on the structure of the compound. The GWP of a compound, as defined by the Intergovernmental Panel on Climate Change (IPCC) in 1990 and updated in 1998 (World Meteorological Organization, *Scientific Assessment of Ozone Depletion:* 1998, Global Ozone Research and Monitoring Project—Report No. 44, Geneva, 1999), is calculated as the warming due to the release of 1 kilogram of a compound relative to the warming due to the release of 1 kilogram of $CO_2$ over a specified integration time horizon (ITH):

$$GWP_x(t') = \frac{\int_0^{ITH} F_x C_{Ox} e^{-t/\tau x} dt}{\int_0^{ITH} F_{CO_2} C_{CO_2}(t) dt}$$

where F is the radiative forcing per unit mass of a compound (the change in the flux of radiation through the atmosphere due to the IR absorbance of that compound), C is the atmospheric concentration of a compound, $\tau$ is the atmospheric lifetime of a compound, t is time and x is the compound of interest (i.e., $C_{Ox}$ is the time 0 or initial concentration of compound x).

The commonly accepted ITH is 100 years representing a compromise between short term effects (20 years) and longer term effects (500 years or longer). The concentration of an organic compound in the atmosphere is assumed to follow pseudo first order kinetics (i.e., exponential decay). The concentration of $CO_2$ over that same time interval incorporates a more complex model for the exchange and removal of $CO_2$ from the atmosphere (the Bern carbon cycle model).

$CF_3CF_2C(O)CF(CF_3)_2$ has an atmospheric lifetime of approximately 5 days based on photolysis studies at 300 nm. Other perfluoroketones show similar absorbances and thus are expected to have similar atmospheric lifetimes. A measured IR cross-section was used to calculate the radiative forcing value for $CF_3CF_2C(O)CF(CF_3)_2$ using the method of Pinnock, et al. (*J. Geophys. Res.*, 100, 23227, 1995). Using this radiative forcing value and the 5 day atmospheric lifetime, the GWP (100 year ITH) for a perfluoroketone with 6 carbon atoms is 1 while the GWP for $C_2F_6$ is 11,400. The perfluoroketones of the invention typically have a GWP less than about 10. As a result of their rapid degradation in the lower atmosphere, the perfluorinated ketones have short lifetimes and would not be expected to contribute significantly to global warming.

Additionally, the fluorinated ketones have low toxicity. For example, the perfluoroketone $CF_3CF_2C(O)CF(CF_3)_2$ has low acute toxicity based on short-term inhalation tests with rats. Based on a four-hour exposure period, the $LC_{50}$ concentration is 100,000-ppm perfluoroketone in air. This toxicity is comparable to that of the perfluorocarbons presently used as cleaning agents in the semiconductor industry.

The following examples further describe the methods of using fluorinated ketones as cleaning agents. The examples are provided for exemplary purposes to facilitate understanding of the invention and should not be construed to limit the invention to the examples. Unless otherwise specified, all percentages and proportions are by weight.

EXAMPLES

Preparation, Sources for Organofluorine Compounds Evaluated

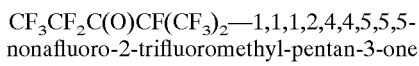
nonafluoro-2-trifluoromethyl-pentan-3-one

Into a clean dry 600 mL Parr reactor equipped with stirrer, heater and thermocouple were added 5.6 g (0.10 mol) of anhydrous potassium fluoride (available from Sigmna Aldrich Chemical Co., Milwaukee, Wis.) and 250 g of anhydrous diglyme (anhydrous diethylene glycol dimethyl ether, available from Sigma Aldrich Chemical Co., Milwaukee, Wis.). The anhydrous potassium fluoride used in this synthesis, and in all subsequent syntheses, was spray dried, stored at 125° C. and ground shortly before use. The contents of the reactor were stirred while 21.0 g (0.13 mol) of $C_2F_5COF$ (approximately 95.0 percent purity available from 3M Company, St. Paul, Minn.) was added to the sealed reactor. The reactor and its contents were then heated, and when a temperature of 70° C. had been reached, a mixture of 147.3 g (0.98 mol) of $C_2$=$CFCF_3$ (hexafluoropropylene, available from Sigma Aldrich Chemical Co.) and 163.3 g (0.98 mol) of $C_2F_5COF$ was added over a 3.0 hour time period. During the addition of the hexafluoropropylene and the $C_2F_5COF$ mixture, the pressure was maintained at less than 95 psig (7500 torr). The pressure at the end of the hexafluoropropylene addition was 30 psig (2300 torr) and did not change over the 45-minute hold period. The reactor contents were allowed to cool and were one-plate distilled to obtain 307.1 g containing 90.6% 1,1,1,2,4,4,5,5,5-nonaflouro-2-triflouromethyl-butan-3-one and 0.37% $C_6F_{12}$ (hexaflouoropropylene dimer) as determined by gas chromatography. The crude fluorinated ketone was water-washed, distilled, and dried by contacting with silica gel to provide a fractionated fluorinated ketone of 99% purity and containing 0.4% hexafluoropropylene dimers.

A fractionated fluorinated ketone made as described above was purified of hexafluoropropylene dimers using the following procedure. Into a clean dry 600 mL Parr reactor equipped with stirrer, heater and thermocouple were added 61 g of acetic acid, 1.7 g of potassium permanganate, and 301 g of the above-described fractionated 1,1,1,2,4,4,5,5,5-nonafluoro-2-trifluoromethyl-butane-3-one. The reactor was sealed and heated to 60° C., while stirring, reaching a pressure of 12 psig (1400 torr). After 75 minutes of stirring at 60° C., a liquid sample was taken using a dip tube, the sample was phase split and the lower phase was washed with water. The sample was analyzed using glc and showed undetectable amounts of hexafluoropropylene dimers and small amounts of hexafluoropropylene trimers. A second sample was taken 60 minutes later and was treated similarly. The glc analysis of the second sample showed no detectable dimers or trimers. The reaction was stopped after 3.5 hours, and the purified ketone was phase split from the acetic acid and the lower phase was washed twice with water. 261 g of the ketone was collected, having a purity greater than 99.6% by glc and containing no detectable hexafluoropropylene dimers or trimers.

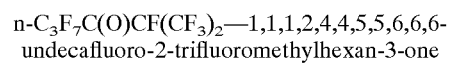
undecafluoro-2-trifluoromethylhexan-3-one

Into a clean dry 600 mL Parr reactor equipped with stirrer, heater and thermocouple were added 5.8 g (0.10 mol) of anhydrous potassium fluoride and 108 g of anhydrous diglyme. The contents of the reactor were stirred and cooled with dry ice while 232.5 g (1.02 mol) of n-$C_3F_7COF$ (available from 3M Co., approximately 95.0 percent purity) was added to the sealed reactor. The reactor and its contents were then heated, and when a temperature of 72° C. had been reached, 141 g (0.94 mol) of hexafluoropropylene was added at a pressure of 85 psig (5150 torr) over a 3.25 hour time period. During the addition of hexafluoropropylene the temperature of the reactor was increased slowly to 85° C. while maintaining the pressure at less than 90 psig (5400 torr). The pressure at the end of the hexafluoropropylene addition was 40 psig (2800 torr) and did not change over an additional 4-hour hold period. The lower phase was fractionally distilled to give 243.5 grams of 1,1,1,2,4,4,5,5,6,6,6-undecafluoro-2-trifluoromethylhexan-3-one, having a boiling point of 72.5° C. and a purity of 99.9% as determined by gas chromatography. The structure was confirmed by gas chromatography and mass spectrometry (GCMS).

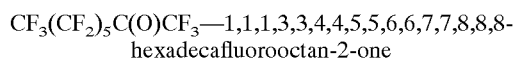
hexadecafluorooctan-2-one 1052 mL of 2-octyl acetate was converted to the perfluorinated ester via direct fluorination as described in U.S. Pat. No. 5,488,142 (Fall et al.). The resulting perfluorinated ester was treated with methanol to convert it to the hemiketal to allow distillation of the reaction solvent. 1272 g of the resulting hemiketal was slowly added to 1200 mL of concentrated sulfuric acid, and the resulting reaction mixture was re-fractionated to yield 1554.3 g of 1,1,1,3,3,4,4,5,5,6,6,7,7,8,8,8-hexadecafluoro-octan-2-one, having a boiling point of 97° C. and having a purity of 98.4% as measured by nuclear magnetic resonance spectroscopy.

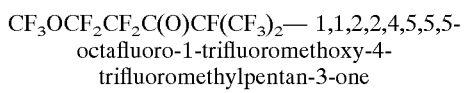
octafluoro-1-trifluoromethoxy-4-trifluoromethylpentan-3-one

Into a clean dry 600 mL Parr reactor were added 11.6 g (0.20 mol) of anhydrous potassium fluoride and 113.5 g of anhydrous diglyme. The contents of the reactor were stirred and cooled with dry ice, then 230 g (0.96 mol) of $CF_3OCF_2CF_2COF$ (available from 3M Co., approximately 97 percent purity) was added to the sealed reactor using isolated vacuum. With the reactor at 80° C. and pressure of 80 psig (4900 torr), 154 g (1.03 mol) of hexafluoropropylene was gradually added over a 3½ hour period. Following a one hour reaction hold time, the product was recovered from the reaction mixture by distillation and phase split prior to fractionation to give 100 g of 1,1,2,2,4,5,5,5-octafluoro-1-trifluoromethoxy-4-trifluoromethylpentan-3-one, having a boiling point of 77° C. and a purity of 99.8% as determined by gas chromatography. The structure was confirmed by gas chromatography and mass spectroscopy.

$ClCF_2C(O)CF(CF_3)_2$—1-chloro-1,1,3,4,4,4-hexafluoro-3-trifluoromethyl-butan-2-one To a clean dry 600 mL Parr pressure reactor was charged 53.5 g (0.92 mol) of anhydrous potassium fluoride, 150 g of anhydrous diglyme and 150 g of chlorodifluoroacetic anhydride. With the reactor set at 80° C. and 92 psig (5500 torr), 123 g (0.820 mol) of hexafluoropropylene was charged over a 3 hour period at a tank pressure not exceeding 120 psig (7000 torr). Following reaction for ½ hour at 80° C., the reactor contents were allowed to cool and were distilled to obtain 180.6 g of crude material. Upon fractional distillation, acetic acid/$KMnO_4$ treatment and refractionation of the crude material, 46.1 g (26% of theoretical yield) of $(CF_3)_2CFC(O)CF_2Cl$, a clear colorless liquid, was obtained having a purity of 98.8% as determined by gas chromatography.

$(CF_3)_2CFC(O)CF(CF_3)_2$— 1,1,1,2,4,5,5,5,6,6,6-octafluoro-2,4-bis(trifluoromethyl)pentan-3-one 8.1 g (0.14 mol) of anhydrous potassium fluoride, 216 g (0.50 mol) of perfluoro(isobutyl isobutyrate) (made by reacting isobutyl isoburyrate with fluorine gas as described in U.S. Pat. No. 5,399,718 (Costello et al.)) and 200 grams of anhydrous diglyme were charged to a clean dry 600 mL Parr pressure reactor. After cooling the reactor to <0° C., 165 g (1.10 mol) of hexafluoropropylene was added to the resulting mixture. The contents in the reactor were allowed to react overnight at 70° C. with stirring, then the reactor was allowed to cool and the excess pressure in the reactor was vented to the atmosphere. The contents of the reactor were then phase split to obtain 362.5 g of lower phase. The lower phase was retained and mixed with lower phases saved from previous analogous reactions. To 604 g of accumulated lower phases containing 22% perfluoroisobutyryl fluoride and 197 g (1.31 mol) of hexafluoropropylene was added 8 g (0.1 mol) of anhydrous potassium fluoride and 50 g of anhydrous diglyme, and the resulting mixture was allowed to react in the Parr reactor in the same manner as before. This time 847 g of lower phase resulted, containing 54.4% of desired material and only 5.7% of perfluoroisobutyryl fluoride. The lower phase was then water washed, dried with anhydrous magnesium sulfate, and fractionally distilled to give 359 g of 1,1,1,2,4,5,5,5,6,6,6-octafluoro-2,4-bis(trifluoromethyl)pentan-3-one having 95.2% purity as determined by gas chromatography and mass spectroscopy ("gcms") (47% theoretical yield) and having a boiling point of 73° C.

$CF_3(CF_2)_5C(O)CF(CF_3)_2$— 1,1,1,2,4,4,4,5,5,6,6,7,7,8,8,9,9,9-heptadecafluoro-2-trifluoromethyl-nonan-3-one A mixture consisting of 2027 g of trifluoroacetic acid pentadecafluoroheptyl ester (made by reacting heptyl acetate with fluorine gas as described in U.S. Pat. No. 5,399,718 (Costello et al.)), 777 g of 3M™ PF-5052 Performance Liquid (a mixture of perfluorinated solvents, available from 3M Company), 3171 g of anhydrous diglyme and 79 g of anhydrous potassium fluoride were added to a 2-gallon (7.6 L) stainless steel stirred pressure vessel. The vessel was heated and 1816 g of hexafluoropropylene was added over a 2-hour period while maintaining a reaction temperature of about 50° C. The vessel was held at 50° C. for an additional 1½ hours after the hexafluoropropylene addition was complete. The reactor was cooled and drained. The resulting liquid was phase split and the lower phase fractionally distilled to give 565 g of 1,1,1,2,4,4,4-heptafluoro-3-trifluoromethyl-butan-2-one having a boiling point of 25° C. and purity of 95% and 1427 g of 1,1,1,2,4,4,5,5,6,6,7,7,8,8,9,9,9-heptadecafluoro-2-trifluoromethyl-nonan-3-one, having a boiling point of 134° C. and a 98.5% purity as determined by gas chromatography and mass spectroscopy.

$C_4F_9OCH_3$—perfluorobutyl methyl ether

3M™ NOVEC™ HFE-7100 specialty liquid (available from 3M Company, St. Paul, Minn.).

$C_4F_9OC_2H_5$—perfluorobutyl ethyl ether

3M™ NOVEC™ HFE-7200 specialty liquid (available from 3M Company).

$C_3F_7CF(OC_2H_5)CF(CF_3)_2$—3-ethoxy-perfluoro(2-methylhexane)

3M™ NOVEC™ HFE-7500 specialty liquid (available from 3M Company).

Example 1 Comparative Examples C1–C3

In Example 1, $CF_3CF_2C(O)CF(CF_3)_2$, a perfluoroketone, was evaluated as a wet cleaning agent for removal of fluoropolymer build-up on quartz gas distribution plate tools removed from Model P-5000 etch chambers commercially used for processing 8 inch (20 cm) wafers (obtained from Applied Materials, Santa Clara, Calif.).

For each evaluation, approximately 500 mL of wet cleaning agent was applied to the tool with polymer build-up, and the tool was allowed to soak at room temperature. After 30 minutes of soak time, an attempt was made to remove the polymer by employing gentle manual scrubbing (i.e., very slight force was applied perpendicular to the tool for five minutes) using a clean room wipe (available from Texwipe, Saddle River, N.J.) wrapped around a ⅛ inch (0.3 cm) thick polytetrafluoroethylene slab. After 30 minutes of soak time, approximately half of the polymer deposit was removed. After an additional 30 minutes of soak (for a total of 60 minutes), essentially all of the polymer deposit was removed by scrubbing.

In Comparative Examples C1–C3, essentially the same evaluation procedure was followed as described in Example 1 except the $CF_3CF_2C(O)CF(CF_3)_2$ was replaced with $C_4F_9OCH_3$, $C_4F_9OC_2H_5$ and $C_3F_7CF(OC_2H_5)CF(CF_3)_2$, respectively. After 60 minutes of soak time, essentially all of the polymer deposit was removed using $C_4F_9OCH_3$, $C_4F_9OC_2H_5$ and $C_3F_7CF(OC_2H_5)CF(CF_3)_2$ solvents (this time no scrubbing was done after 30 minutes of soak time).

Examples 2–8

In Examples 2–8, the following fluorinated ketones were evaluated at room temperature as wet cleaning agents: n-$C_3F_7C(O)CF(CF_3)_2$ (Example 2), $CF_3(CF_2)_5C(O)CF_3$ (Example 3), $CF_3OCF_2CF_2C(O)CF(CF_3)_2$ (Example 4), $ClCF_2C(O)CF(CF_3)_2$ (Example 5), $(CF_3)_2CFC(O)CF(CF_3)_2$ (Example 6), $CF_3(CF_2)_5C(O)CF(CF_3)_2$ (Example 7) and $CF_3CF_2C(O)CF(CF_3)_2$ (Example 8—same ketone as used in Example 1). Each ketone was evaluated for its ability to clean chamber gas shower heads contaminated with fluoropolymer from commercial operation (contaminated heads obtained from Tokyo Electron Ltd., Tokyo, Japan). For each cleaning test, approximately 20 mL of each solvent was used to clean except for $ClCF_2C(O)CF(CF_3)_2$, in which case 40 mL of the solvent was used to allow for that solvent's higher volatility. A portion of each contaminated gas shower head was soaked in the test fluorinated ketone solvents for about 5 minutes and then was gently scrubbed manually with a ⅛ (0.3 cm) thick polytetrafluoroethylene slab wrapped with a clean room wipe as described in Example 1. As polymer removal was somewhat difficult in each case, each contaminated shower head was soaked for an additional 5 minutes in the test fluorinated ketone solvents (for a total of 10 minutes of immersion) and was scrubbed again. This time, the fluoropolymer was easily removed from the contaminated head with all the fluorinated ketone test solvents.

Examples 9–10

$CF_3CF_2C(O)CF(CF_3)_2$ was evaluated further evaluated as a cleaning solvent at 40° C. (Example 9) and at a few degrees below its boiling point (Example 10). Polymer removal rate increased with increasing solvent temperature.

From the foregoing detailed description it will be evident that modifications can be made in the methods of the methods of the invention without departing from the spirit or scope of the invention. Therefore, it is intended that all modifications and variations not departing from the spirit of the invention come within the scope of the claims and their equivalent.

We claim:

1. A method of cleaning a vapor reactor comprising removing residue from said vapor reactor by contacting said vapor reactor with a cleaning agent, said cleaning agent comprising a liquid fluorinated ketone having 5 to 10 carbon atoms and up to two hydrogen atoms.

2. The method of claim 1, wherein fluorinated ketone has 5 to 7 carbon atoms.

3. The method of claim 1, wherein fluorinated ketone further has up to two halogen atoms selected from the group consisting of chlorine, bromine, iodine, and a mixture thereof.

4. The method of claim 1, wherein fluorinated ketone further contains one or more heteroatoms interrupting the carbon atoms, said heteroatoms selected from the group consisting of oxygen, nitrogen, and sulfur.

5. The method of claim 1, wherein fluorinated ketone is a perfluoroketone.

6. The method of claim 1, wherein fluorinated ketone is $n-C_3F_7C(O)CF(CF_3)_2$.

7. The method of claim 1, wherein fluorinated ketone is $CF_3C(O)(CF_2)_5CF_3$.

8. The method of claim 1, wherein fluorinated ketone is $CF_3OCF_2CF_2C(O)CF(CF_3)_2$.

9. The method of claim 1, wherein fluorinated ketone is $ClCF_2C(O)CF(CF_3)_2$.

10. The method of claim 1, wherein fluorinated ketone is $(CF_3)_2CFC(O)CF(CF_3)_2$.

11. The method of claim 1, wherein fluorinated ketone is $CF_3(CF_2)_5C(O)CF(CF_3)_2$.

12. The method of claim 1, wherein fluorinated ketone is a $CF_3CF_2C(O)CF(CF_3)_2$.

13. The method of claim 1, wherein the cleaning agent further comprises an auxiliary cleaning agent selected from the group consisting of a hydrofluorocarbon, hydrochlorofluorocarbon, perfluorocarbon, perfluoropolyether, hydrofluoroether, hydrofluoropolyether, hydrochlorofluoroether, fluorinated aromatic compound, chlorofluorocarbon, bromofluorocarbon, bromochlorofluorocarbon, hydrobromocarbon, iodofluorocarbon, hydrobromofluorocarbon, and mixtures thereof.

14. The method of claim 1, wherein fluorinated ketone has a boiling point up to about 150° C.

15. The method of claim 5, wherein perfluoroketone is selected from the group consisting of $CF_3CF_2C(O)CF(CF_3)_2$, $CF_3C(O)CF(CF_3)_2$, $(CF_3)_2CFC(O)CF(CF_3)_2$, $CF_3(CF_2)_2C(O)CF(CF_3)_2$, $CF_3OCF_2CF_2C(O)CF(CF_3)_2$, perfluorocyclopentanone, perfluorocyclohexanone, $CF_3CF_2C(O)CF_2CF_2CF_3$, $CF_3OCF_2CF_2C(O)CF(CF_3)_2$, $CF_3OCF_2C(O)CF(CF_3)_2$, and mixtures thereof.

16. The method of claim 13, wherein the auxiliary cleaning agent is a hydrofluoroether.

17. The method of claim 16, wherein the hydrofluoroether is selected from the group consisting of $C_4F_9OCH_3$, $C_4F_9OC_2H_5$, $C_3F_7CF(OC_2H_5)CF(CF_3)_2$, and mixtures thereof.

* * * * *

UNITED STATES PATENT AND TRADEMARK OFFICE
CERTIFICATE OF CORRECTION

PATENT NO. : 6,394,107 B1
DATED : May 28, 2002
INVENTOR(S) : Kesari, Susrut

It is certified that error appears in the above-identified patent and that said Letters Patent is hereby corrected as shown below:

Title page,
Item [56], the asterisk "*" should be removed from all patents cited, except
JP 200-248363 9/2000

Column 1,
Line 45, "hydrofluoro" should read -- hydrofluoro- --

Column 2,
Line 39, "by-product" should read -- by-products --

Column 3,
Line 53, "perfluorocarbon" should read -- perfluorocarboxylic --
Lines 53 and 54, "perfluorocarbon" should read -- perfluorocarbonyl --

Column 5,
Line 41, "scaled" should read -- sealed --

Column 9,
Lines 8 and 9, "1/8 (0.3 cm)" should read -- 1/8 inch (0.3 cm) --
Lines 37, 39 and 43, "wherein fluorinated" should read -- wherein said liquid fluorinated --

Column 10,
Lines 3, 5, 7, 9, 11, 13, 15, 17 and 28, "wherein fluorinated" should read -- wherein said liquid fluorinated --
Line 18, "a" should be deleted Signed and Sealed this Twenty-seventh Day of May, 2003

JAMES E. ROGAN
*Director of the United States Patent and Trademark Office*